United States Patent [19]

Sarumaru et al.

[11] Patent Number: 4,604,370
[45] Date of Patent: Aug. 5, 1986

[54] PROCESS FOR REGENERATING A CATALYST

[75] Inventors: Kohei Sarumaru, Ami; Takeshi Shibano, Yokkaichi; Yoichi Ishii; Etsuji Yamamoto, both of Ami, all of Japan

[73] Assignee: Mitsubishi Petrochemical Company, Limited, Tokyo, Japan

[21] Appl. No.: 753,136

[22] Filed: Jul. 9, 1985

[30] Foreign Application Priority Data

Jul. 23, 1984 [JP] Japan ................................. 59-152651

[51] Int. Cl.$^4$ .......................... R01J 23/92; C07C 45/35
[52] U.S. Cl. .......................... 502/38; 502/52; 568/477; 568/479; 568/480
[58] Field of Search .................. 502/38, 41, 45–49, 502/52, 56, 205

[56] References Cited

U.S. PATENT DOCUMENTS

| 4,052,333 | 10/1977 | Lee | 502/51 |
| 4,148,757 | 4/1979 | Brazdil et al. | 502/205 |
| 4,284,583 | 8/1981 | Pujado | 502/38 |

*Primary Examiner*—P. E. Konopka
*Attorney, Agent, or Firm*—Oblon, Fisher, Spivak, McClelland & Maier

[57] ABSTRACT

A process for regenerating a Mo.Bi-based multi-oxide catalyst the catalytic performance of which has deteriorated as a result of its use in vapor-phase catalytic oxidation of propylene or isobutene to prepare acrolein or methacrolein, respectively, which process comprises: heating the deteriorated Mo.Bi-based multi-oxide catalyst in an atmosphere consisting essentially of air at a temperature of 380° C. to 540° C., so as to attain at least partial restoration of the catalytic performance thereof.

6 Claims, No Drawings

PROCESS FOR REGENERATING A CATALYST

BACKGROUND OF THE INVENTION

1. Field of the Art

The present invention relates to a process for regenerating a Mo.Bi-based multi-oxide catalyst which has been used in a specific reaction, i.e., a reaction of formation of acrolein or methacrolein by vapor-phase catalytic oxidation of propylene or isobutene.

Mo.Bi-based multi-oxide catalysts are widely known to be useful for selective oxidation reaction of propylene or isobutene into acrolein or methacrolein, respectively, ammoxidation reaction of propylene and ammonia, or isobutene and ammonia into acrylonitrile or methacrylonitrile, respectively, and oxidative dehydrogenation reaction of butane into butadiene, and are being industrially used.

When, among these reactions, the selective oxidation reaction of olefins to aldehydes is compared with the ammoxidation reaction of olefins to nitriles, it may be said that the former is generally carried out at a temperature of approximately 260° C. to 360° C. in the presence of a catalyst in the form of a fixed bed, while the latter is generally carried out at a temperature of approximately 360° C. to 460° C. in the presence of a catalyst in the form of a fluidized bed. This difference in operational method is attributable to the characteristics of each reaction.

The catalyst to be subjected to such vapor phase catalytic reaction is used for a relatively long period of time. When the catalytic performance of the catalyst degenerates or deteriorates to a certain degree, the used catalyst is replaced with a fresh catalyst from an economical point of view. The used catalyst is ordinarily subjected to a process for recovering the metal contained therein.

It is well known that the deterioration of the catalytic performance of Mo Bi-based multi-oxide catalysts used for these vapor phase catalytic reactions has almost no causative relation to the deposition of coke on the catalysts but occurs mainly because of the loss of Mo by sublimation.

2. Prior Art

For these reasons, care has been taken in industrial processes using Mo.Bi-based multi-oxide catalysts to carry out measures such as reducing the reaction temperature as much as possible and reducing the partial pressure of steam as much as possible. Methods have also been proposed to regenerate the deteriorated Mo.-Bi-based multi-oxide catalysts. That is, these methods are described in Japanese Patent Laid-Open Publication Nos. 50-49201, and 57-56044, Japanese Patent Publication No. 55-49541, U.S. Pat. No. 4,052,332, West Germany Patent Laid-Open Publication No. 3,311,521, and East Germany Pat. No. 137,889.

It is understood that these methods are all directed to catalysts used in an ammoxidation reaction, and it is considered logical that these methods aim at regenerating such catalysts. If it is supposed that the catalyst degeneration is due to the sublimation of Mo, the ammoxidation reaction must involve remarkable sublimation of Mo because it is carried out at a relatively high temperature as described hereinabove.

These regeneration methods are all characterized in that Mo in an amount corresponding to that of Mo lost by sublimation from the catalyst is added to the deteriorated catalyst by any suitable method, and the resultant catalyst is subjected to heat treatment, or Mo in an amount corresponding to that of Mo lost is added to the deteriorated catalyst together with other catalytic components (Bi, Cr, Mn, Fe, Co, Ni, etc.), and the resultant catalyst is subjected to heat treatment. Such a regeneration principle can be well understood in consideration of the fact that the main cause of the catalyst deterioration resides in sublimation of Mo.

However, as far as we know, it is considered that these regeneration methods are not always satisfactory from the point of view of industrial practice.

SUMMARY OF THE INVENTION

As described hereinabove, the selective oxidation reaction of olefins to unsaturated aldehydes is carried out at a temperature about 100° C. lower than that for the ammoxidation reaction of this type of olefins to unsaturated nitriles. With this reaction difference in view, the present invention contemplates conducting the regeneration of the catalyst by using heat treatment in place of the regeneration principle of resupplying the lost Mo.

Thus, the process for the regeneration of a catalyst according to the present invention comprises heating a Mo.Bi-based multi-oxide catalyst the catalytic performance of which has deteriorated as a result of its use in the vapor phase catalytic oxidation of propylene or isobutene to prepare acrolein or methacrolein, respectively, in an atmosphere consisting essentially of air at a temperature of 380° C. to 540° C., so as to attain at least partial restoration of the catalytic performance thereof.

In accordance with the present invention, the catalytic performance of deteriorated catalysts can be restored by a simple treatment, i.e., heating. Since the selective oxidation reaction of olefins to unsaturated aldehydes is carried out at a relatively low temperature, it is naturally expected that the loss of Mo will be small. However, judging from the fact that the deterioration of this type of catalyst is considered to be due to the loss of Mo, and regeneration methods comprising resupplying the lost Mo have been proposed, it can be said that the realization of catalyst regeneration without the resupply of Mo is an unexpected discovery.

As described hereinabove, the catalytic oxidation of olefins to unsaturated aldehydes is generally carried out by using the catalyst as a fixed bed. The regeneration method of the present invention can be carried out while the deteriorated catalyst is maintained in the fixed bed state. Since the catalyst fixed bed is provided with a heating and cooling device, heating for the regeneration of the deteriorated catalyst can be very simply carried out by employing the device. In accordance with this mode of practice wherein the deteriorated catalyst present in the fixed bed is regenerated in the catalytic reaction apparatus, not only is the regeneration process itself simple, but removal of the deteriorated catalyst for regeneration is also unnecessary. This further increases the advantages of the regeneration method of the present invention. Furthermore, it is to be understood that the regeneration method of the present invention can be carried out after the deteriorated catalyst has been removed from the catalytic reaction apparatus.

The catalytic activity of the regenerated catalyst is stable over a long period of time.

DETAILED DESCRIPTION OF THE INVENTION

Basic Investigation

As described hereinabove, since the selective oxidation reaction of olefins to unsaturated aldehydes is carried out at a relatively low temperature, it was observed that even if the catalyst is used in the presence of steam for several years, the amount of Mo lost due to its sublimation from the catalyst is at the most only several % (hereinafter, % by weight) of the total content of the Mo.

On the other hand, in order to investigate how the content of Mo in a catalyst fresh from preparation influences the initial reaction activity of the catalyst, several types of catalysts differing only in Mo content were prepared and the catalytic performances of these catalysts were investigated. It was observed that the initial catalytic performance of a catalyst having the optimum Mo content was very close to that of a catalyst whose Mo content is the optimum Mo content minus several percentages which have been lost during its use for several years, and the reduction in catalytic performance of the latter catalyst was not so large as that of the deteriorated catalyst.

This apparently contradictory relationship was easily clarified by analyzing the surface composition of the catalyst by means of ESCA. That is, even if the amount of Mo is reduced by a number of % when the catalyst is prepared, the amount of Mo present in the surface portion of the catalyst undergoes almost no change, whereas, in the case of the catalyst used for a long period of time, a reduction of the surface Mo content of over 10% was observed as compared with a fresh catalyst. This indicates that notwithstanding the fact that the amount of Mo lost of the deteriorated catalyst is only a number of %, the loss of Mo occurred mainly in the surface portion of the catalyst particles, i.e., only Mo present in the vicinity of the catalyst surface was sublimed.

This fact is remarkably different from a case where the catalyst is used at a high temperature, such as that in an ammoxidation reaction. That is, at such a high temperature, the rate of diffusion of Mo in the catalyst particles (solid phase diffusion) is high, and Mo in the interior of the particle largely participates in the loss of Mo due to its sublimation. In the case of the selective oxidation reaction with which the present invention is concerned, the rate of diffusion of Mo in the catalytic particle is low because of the lower temperature reaction, and the rate of sublimation of Mo in the surface layer of the catalyst particle is relatively high, with the result that a large concentration gradient of Mo is present from the surface to the interior of the catalyst particle. Therefore, it is understandable that, in the selective oxidation reaction to which the present invention is directed, although the amount of Mo lost is only a number of % of the total amount of Mo, the catalytic performance deteriorates to the same degree as in the case where over 10% of Mo is lost.

It follows from the results of the above mentioned basic investigation that the regeneration of a deteriorated catalyst used in the selective oxidation reaction of olefins to unsaturated aldehydes can be carried out to a satisfactory degree by subjecting the catalyst to high temperature heat treatment, wherein the resupply of Mo occurs due to the diffusion of Mo in the interior of the catalyst particle into the surface portion thereof, without resupplying Mo from the outside. It can be said that this is preferable.

Regeneration Treatment

The regeneration process according to the present invention comprises heating a Mo.Bi-based multi-oxide catalyst in a non-reducing atmosphere consisting essentially of air at a temperature of 380° C. to 540° C.

The heating atmosphere "consisting essentially of air" means that the atmosphere, in addition to consisting of only a gaseous mixture of pure air composition, may further contain a small amount of carbon dioxide, steam, nitrogen gas, or the like and may contain an additional amount of pure oxygen. Since the rate of solid phase diffusion of Mo is increased as the ionic radius is decreased, it is preferable that the Mo be in a high-order oxide state. Therefore, the degree of "small amount" for the above mentioned non-oxidizing gas components is determined from this point of view. Furthermore, since the "atmosphere" should only have an oxidizing property sufficient to be capable of preventing reduction of the Mo, it includes both the case where air is in a flowing state and the case where air is in a stagnant state (including, of course, a combination of the two states).

In addition, since the regeneration treatment is carried out until the catalytic performance of the deteriorated catalyst is at least partially restored, it is not necessary to maintain this atmosphere throughout the heating process as long as such a restoration state is realized. Therefore, for example, it is possible to carry out the former part of the heating process in the above mentioned atmosphere and the latter part thereof in a non-reducing atmosphere. A heating atmosphere containing a stream of steam at a high temperature in a high concentration should be avoided from the point of view of preventing sublimation of Mo.

The heating temperature is in the range of from 380° C. to 540° C., preferably from 390° C. to 530° C. We have found that if the heating temperature is less than 380° C., sufficient diffusion of Mo through the catalyst particle cannot be realized. On the other hand, if the heating temperature is higher than 540° C., a reduction in the catalytic activity due to the sintering of the catalyst will begin to appear. The heating temperature should not be constant throughout the regeneration treatment.

The heating in the regeneration is carried out until the deteriorated catalytic performance is at least partially restored. The "catalytic performance" as used herein is preferably evaluated by the total of the yield of the desired unsaturated aldehyde and the yield of the corresponding unsaturated carboxylic acid which is inevitably formed. Although the heating should be carried out until the catalytic performance is at least partially restored, it is obivious that it is desirably carried out until maximum restoration is attained.

The heating period varies with the degree of deterioration and the desired degree of restoration of the catalyst. Generally, low temperature heating requires a long period of time and high temperature heating requires only a short period of time. More specifically, for example, at a heating temperature of less than 500° C., the heating time is at least 12 hours, preferably at least 24 hours, more preferably from a number of days to over ten days. At a heating temperature of 500° C. or more, the heating time is at least 2 hours, preferably from over ten hours to a number of hours.

The heating for regeneration may be applied to the deteriorated catalyst after it has been removed from the catalytic oxidation reaction. Otherwise, it may be applied to the deteriorated catalyst retained, especially as the fixed bed, in the apparatus.

The heating means may be any means capable of maintaining the solid in the form of particles at the desired temperature. More specifically, the deteriorated catalyst particles are brought into contact with a source of heat such as heated gas (that is, heated "atmosphere consisting essentially of air") and a heated solid surface.

Mo.Bi-based Multi-oxide Catalyst and Reaction

As described hereinabove, Mo.Bi-based multi-oxide catalysts and the selective oxidation of olefins to unsaturated aldehyde in which the above-mentioned catalysts are used are well known.

Generally, the Mo.Bi-based multi-oxide catalysts can be conceptionally represented by the following formula:

$$Mo_aBi_bX_cO_d,$$

wherein: X represents a metal or metalloid or nonmetallic component other than Mo and Bi and is, for example, selected from the group consisting of Fe, Co, Ni, Mn, W, alkali metals, Tl, alkaline earth metals, B, P, As and Si; a, b and c represent the numbers of Mo, Bi and X atoms, respectively; and d is a value determined by the oxide state of these components. Examples of such multi-oxide catalysts are disclosed in, for example, Japanese Patent Laid-Open Publication Nos. 47-17711, 47-27490, 47-41329, 47-42241, 47-42813, 48-1645, 48-4763, 48-4764, 48-4765, 55-46374, 55-45048, 55-45256, 57-50765, 57-56373, and 58-4691.

Examples of the selective oxidation of propylene or isobutene to acrolein or methacrolein, respectively, wherein the above mentioned catalysts are used are disclosed in the above mentioned publications and Japanese Patent Laid-Open Publication Nos. 59-76541, 59-46132, and 58-143843, and Japanese Patent Publication No. 58-49535. The catalyst is generally used in the form of a fixed bed. Although this reaction is selective oxidation, the corresponding unsaturated carboxylic acid is inevitably by-produced, and this byproduct is also a useful product.

EXPERIMENTAL EXAMPLES

REFERENCE EXAMPLE 1

A catalyst having the following compositional ratio was prepared according to a conventional method.

$$Mo_{12}Bi_5Ni_3Co_2Fe_{0.4}Na_{0.2}B_{0.4}K_{0.1}Si_{24}O_x$$

wherein x is a value determined by the oxide state of the metallic elements.

The selective oxidation reaction of propylene was carried out by using 50 ml of this catalyst. The reaction vessel used was a stainless-steel tube reactor having an inner diameter of 21.2 mm and a length of 500 mm and provided with a niter bath. The feed composition was 90 mol % propylene, 30 mol % steam and 61 mol % air. The reaction bath temperature was 305° C.; the reaction pressure was 1 kg/cm²G; and the contact time was 5.3 seconds. As a result of the reaction, the conversion of propylene was 98.6%, and the total yield of acrolein and acrylic acid was 91.8%.

REFERENCE EXAMPLE 2

After the above described catalyst was used in a large amount under the temperature condition of a reaction temperature of 305° C. to 320° C. for several years, the catalyst was removed from the reactor as a deteriorated catalyst. This catalyst was thoroughly mixed, and part of the mixed catalyst was used to carry out the same reaction as that described in Reference Example 1. However, in this case, the reaction bath temperature was 320° C.

As a result, the conversion of propylene was 98.3%, and the total yield of acrolein and acrylic acid was 88.6%.

EXAMPLE 1

A part of the removed catalyst mixture as stated in Reference Example 2 was heat treated at a temperature of 540° C. for 3 hours under an air atmosphere by using a muffle furnace.

With the use of this treated catalyst, selective oxidation reaction of propylene was carried out under the same conditions as those described in Reference Example 2. As a result, the conversion of propylene was 98.1%, and the total yield of acrolein and acrylic acid was 91.4%.

EXAMPLE 2

A part of the removed catalyst mixture described in Reference Example 2 was heat treated at a temperature of 470° C. for 3 days under the condition of a space velocity (SV) of 10 hr⁻¹ in an aerated furnace with a jacket of a molten salt medium.

With this catalyst, selective oxidation reaction of propylene was carried out under the same conditions as those described in Reference Example 2. As a result, the conversion of propylene was 98.3%, and the total yield of acrolein and acrylic acid was 91.1%.

EXAMPLE 3

A part of the removed catalyst mixture described in Reference Example 2 was heat treated at a temperature of 410° C. for 11 days under the condition of SV of 10 hr⁻¹ in an aerated furnace with a nitrate heating means.

With this catalyst, selective oxidation reaction of propylene was carried out under the same reaction conditions as those described in Reference Example 2. As a result, the conversion of propylene was 98.5%, and the total yield of acrolein and acrylic acid was 90.1%.

EXAMPLE 4

A portion of the removed catalyst mixture described in Reference Example 2 was heat treated at a temperature of 410° C. for 30 days in an aerated furnace with a nitrate heating means. In this case, however, the air was caused to flow at a SV of 10 hr⁻¹ only in the stage of temperature elevation, after which the air flow was stopped.

With this catalyst selective oxidation reaction of propylene was carried out under the same reaction conditions as those described in Reference Example 2. As a result the conversion of propylene was 98.8%, and the total yield of acrolein and acrylic acid was 91.2%.

COMPARATIVE EXAMPLE 1

A portion of the removed catalyst mixture described in Reference Example 2 was heat treated at a temperature of 600° C. for 4 hours under an air atmosphere by using a muffle furnace. With this catalyst selective oxidation reaction of propylene was carried out under the same reaction conditions as those described in Reference Example 2. As a result the conversion of propylene was 94.9%, and the total yield of acrolein and acrylic acid was 88.4%.

COMPARATIVE EXAMPLE 2

A portion of the removed catalyst mixture described in Reference Example 2 was heat treated at a temperature of 350° C. for 10 days under the condition of SV of 1 hr$^{-1}$ in an aerated furnace with a nitrate heating means while air was caused to flow therethrough.

By using this catalyst, selective oxidation reaction of propylene was carried out. As a result the conversion of propylene was 98.5%, and the total yield of acrolein and acrylic acid was 88.9%.

EXAMPLE 5

Using 250 ml of the catalyst as indicated in Reference Example 1, selective oxidation reaction of propylene was continuously carried out for a long period of time in a stainless-steel tube reactor having an inner diameter of 20 mm and a length of 2,200 mm and provided with a niter bath. The composition of the feed gas was 10 mol % propylene, 17 mol % steam and 73 mol % air. The reaction inlet pressure was 1.0 kg/cm$^2$G, and the contact time was 4.0 seconds. At the start of the reaction, at a reaction bath temperature of 318° C., the conversion of propylene was 98.0%, and the total yield of acrolein and acrylic acid was 91.4%. As a result of the continuous operation for several years at a reaction bath temperature of 330° C. the conversion of propylene was 98.2%, and the total yield of acrolein and acrylic acid was 88.2%, which indicated the deterioration of the catalytic performance.

Next, this catalyst without being discharged from the reactor tube was maintained at 450° C. in a molten salt heating medium under an air atmosphere for 7 days.

Thereafter, the catalytic performance was investigated under the above-mentioned reaction conditions. As a result, at a reaction bath temperature of 325° C., the conversion of propylene was 98.1%, and the total yield of acrolein and acrylic acid was 91.0%. Furthermore, in order to confirm the stability of the restored catalytic performance, the continuous operation was continued for about one year. After one year, the catalytic performance at a reaction bath temperature of 328° C. was such that the conversion of propylene was 98.0%, and the total yield of acrolein and acrylic acid was 90.7%.

What is claimed is:

1. A process for regenerating a Mo.Bi-based multi-oxide catalyst which is used in the vapor-phase catalytic oxidation of propylene or isobutene into acrolein or methacrolein, respectively, the catalytic performance of which has deteriorated as a result of the use thereof in the vapor-phase oxidation at least partly because of sublimation of a portion of the molybdenum content of the catalyst, which process comprises:

heating the deteriorated Mo.Bi-based multi-oxide catalyst in an atmosphere consisting essentially of air at a temperature of 380° C. to 540° C., with the proviso that when the temperature ranges from 380° to 500° C., the heating is conducted for at least 12 hours and when the temperature ranges from 500° C. to 540° C., the heating is conducted for at least 2 hours, thereby restoring at least a portion of the performance capability of the catalyst.

2. The process of claim 1, wherein the vapor-phase catalytic oxidation is conducted over a fixed catalyst bed, and wherein the catalyst is regenerated by the prescribed treatment while in the state of a fixed bed.

3. The process of claim 1, wherein said catalyst has the formula: Mo$_a$Bi$_b$X$_c$O$_d$, wherein X is a metal or metalloid other than Mo and Bi, a, b and c respectively represent the number of atoms of Mo, Bi and X in the catalyst and d is the number of oxygen atoms in the catalyst which is determined by the oxidation state of the Mo, Bi and X atoms.

4. The process of claim 3, wherein X is a metal selected from the group consisting of Fe, Co, Ni, Mn, W, alkali metals, Tl, alkaline earth metals, B, P, As and Si.

5. The process of claim 1, wherein the loss of the molybdenum content of the catalyst during the oxidation reaction by sublimation occurs substantially only from the surface particles of the catalyst, and wherein restoration of the performance of the catalyst is at least partially due to a replenishment of the surface molybdenum atoms which have been lost by molybdenum atoms from the interior particles of the catalyst.

6. The process of claim 1, wherein said atmosphere employed doing said catalyst restoration step further comprises oxygen added to the atmosphere.

* * * * *